(12) United States Patent
Gooie

(10) Patent No.: US 11,738,194 B2
(45) Date of Patent: Aug. 29, 2023

(54) CLOSED LOOP COMPUTER-BRAIN INTERFACE DEVICE

(71) Applicant: CereGate GmbH, Munich (DE)

(72) Inventor: Saman Hagh Gooie, Hamburg (DE)

(73) Assignee: CereGate GmbH, Munich (DE)

( * ) Notice: Subject to any disclaimer, the term of this patent is extended or adjusted under 35 U.S.C. 154(b) by 149 days.

(21) Appl. No.: 17/028,061

(22) Filed: Sep. 22, 2020

(65) Prior Publication Data

US 2022/0054830 A1 Feb. 24, 2022

(30) Foreign Application Priority Data

Aug. 21, 2020 (DE) .......................... 102020210676.2

(51) Int. Cl.
*A61N 1/36* (2006.01)
*A61N 1/05* (2006.01)
*G06F 3/01* (2006.01)

(52) U.S. Cl.
CPC ....... *A61N 1/36003* (2013.01); *A61N 1/0531* (2013.01); *A61N 1/0534* (2013.01);
(Continued)

(58) Field of Classification Search
CPC .............. A61N 1/36003; A61N 1/0531; A61N 1/0534; A61N 1/36132; A61N 1/36139;
(Continued)

(56) References Cited

U.S. PATENT DOCUMENTS

| 4,441,202 A | 4/1984 | Tong et al. |
| 4,445,512 A | 5/1984 | Krupka et al. |

(Continued)

FOREIGN PATENT DOCUMENTS

| DE | 102019202666 A1 | 8/2020 |
| DE | 102019209096 A1 | 12/2020 |

(Continued)

OTHER PUBLICATIONS

First Office Action dated Oct. 16, 2019 for German Application No. DE 10 2019 202 666.4, 14 pgs.

(Continued)

*Primary Examiner* — Paula J Stice
(74) *Attorney, Agent, or Firm* — Kowert, Hood, Munyon, Rankin & Goetzel, P.C.

(57) ABSTRACT

The present invention relates to a closed loop computer brain interface device for an individual comprising a receiver module configured to obtain at least one sensor signal indicative of a movement or action of the individual, a processing module operably connected to the receiver module and configured to determine at least one neuronal feedback signal based at least in part on the obtained sensor signal and a transmitter module operably connected to the processing module and configured to transmit the determined neuronal feedback signal to a neurostimulation device of the individual or a neurostimulation module operably connected to the processing module, wherein the neuronal feedback signal is configured to elicit a sensory percept in the cortex of the individual via stimulating afferent sensory axons of the central nervous system targeting sensory neurons of the cortex of the individual and wherein the elicited sensory percept indicates movement support information related to the obtained sensor signal to support the execution of the movement or action of the individual.

Figure 1:
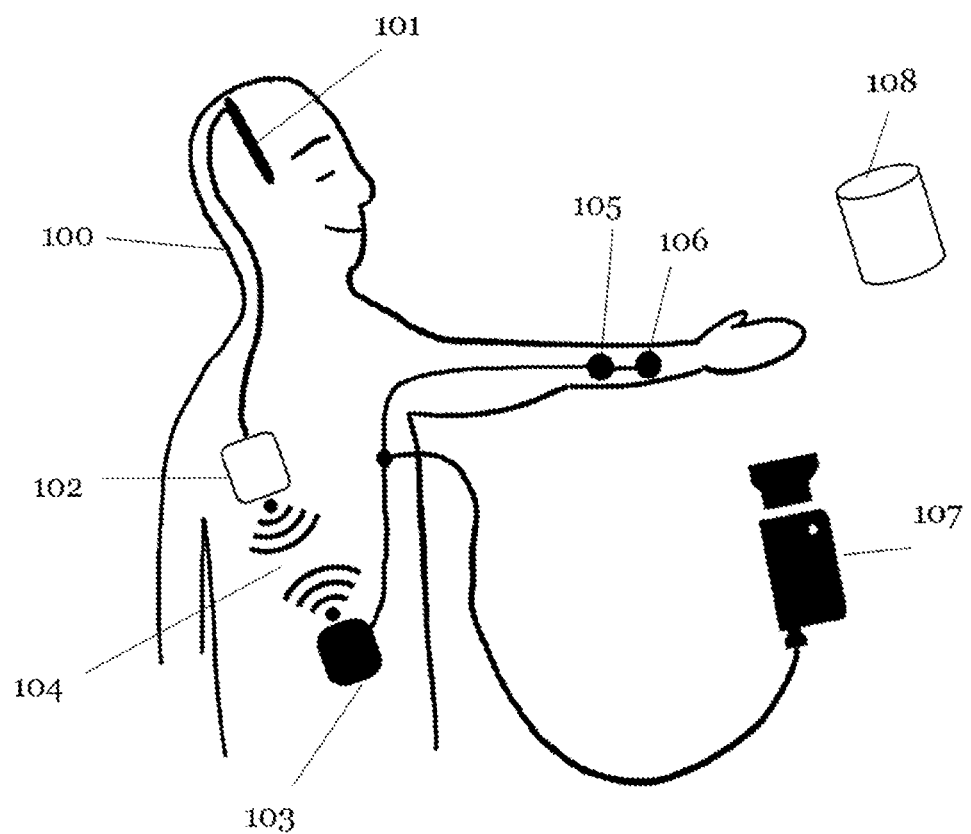

The present invention further relates to a computer program comprising instructions for implementing a closed loop computer brain interface device when being executed by signal processing and transceiver modules of a signal and data processing device, a neuronal stimulation device or system.

20 Claims, 13 Drawing Sheets

(52) U.S. Cl.
CPC ..... *A61N 1/36132* (2013.01); *A61N 1/36139* (2013.01); *A61N 1/36175* (2013.01); *G06F 3/014* (2013.01); *G06F 3/015* (2013.01)

(58) Field of Classification Search
CPC .. A61N 1/36175; A61N 1/36067; G06F 3/015
See application file for complete search history.

(56) References Cited

U.S. PATENT DOCUMENTS

| | | |
|---|---|---|
| 4,488,555 A | 12/1984 | Imran |
| 5,800,535 A | 9/1998 | Howard, III |
| 6,400,989 B1 | 6/2002 | Eckmiller |
| 7,751,884 B2 | 7/2010 | Ternes et al. |
| 7,774,056 B2 | 8/2010 | Torgerson |
| 8,193,766 B2 | 6/2012 | Rondoni et al. |
| 8,290,596 B2 | 10/2012 | Wei et al. |
| 8,352,029 B2 | 1/2013 | Ternes et al. |
| 8,364,271 B2 | 1/2013 | De Ridder |
| 8,380,314 B2 | 2/2013 | Panken et al. |
| 8,423,145 B2 | 4/2013 | Pless et al. |
| 8,437,858 B2 | 5/2013 | Dapper et al. |
| 8,475,172 B2 | 7/2013 | Lieberman et al. |
| 8,494,633 B2 | 7/2013 | Tobacman |
| 8,509,904 B2 | 8/2013 | Rickert et al. |
| 8,812,128 B2 | 8/2014 | Kothandaraman |
| 9,095,314 B2 | 8/2015 | Osorio et al. |
| 9,314,190 B1 * | 4/2016 | Giuffrida ............ A61M 5/1723 |
| 9,357,938 B2 | 6/2016 | Ang et al. |
| 9,526,896 B2 | 12/2016 | Greenberg et al. |
| 9,636,497 B2 | 5/2017 | Bradley et al. |
| 9,713,720 B2 | 7/2017 | Zhu |
| 9,974,478 B1 | 5/2018 | Brokaw et al. |
| 10,568,559 B2 | 2/2020 | Parker et al. |
| 2003/0065366 A1 | 4/2003 | Merritt et al. |
| 2006/0129205 A1 | 6/2006 | Boveja et al. |
| 2006/0241717 A1 | 10/2006 | Whitehurst et al. |
| 2006/0241718 A1 | 10/2006 | Tyler et al. |
| 2007/0027397 A1 | 2/2007 | Fischell et al. |
| 2007/0250134 A1 | 10/2007 | Miesel et al. |
| 2008/0129517 A1 | 6/2008 | Crosby et al. |
| 2008/0139954 A1 | 6/2008 | Day et al. |
| 2009/0264789 A1 | 10/2009 | Molnar et al. |
| 2009/0306741 A1 | 12/2009 | Hogle et al. |
| 2010/0057161 A1 | 3/2010 | Machado et al. |
| 2010/0094382 A1 | 4/2010 | Pezaris et al. |
| 2010/0249879 A1 | 9/2010 | Bracker et al. |
| 2013/0150914 A1 | 6/2013 | Kelly et al. |
| 2013/0253299 A1 | 9/2013 | Weber et al. |
| 2014/0081348 A1 | 3/2014 | Fischell |
| 2014/0379046 A1 | 12/2014 | Tcheng et al. |
| 2015/0018724 A1 | 1/2015 | Hsu et al. |
| 2015/0073492 A1 | 3/2015 | Kilgard et al. |
| 2015/0290453 A1 | 10/2015 | Tyler et al. |
| 2016/0022992 A1 | 1/2016 | Franke et al. |
| 2016/0121118 A1 | 5/2016 | Franke et al. |
| 2017/0182328 A1 | 6/2017 | Moffitt |
| 2018/0050198 A1 | 2/2018 | Mazanec et al. |
| 2019/0030338 A1 | 1/2019 | Wu et al. |
| 2020/0269049 A1 | 8/2020 | Varkuti |

FOREIGN PATENT DOCUMENTS

| | | |
|---|---|---|
| EP | 2552304 B1 | 9/2015 |
| EP | 3229893 A1 | 10/2017 |
| EP | 3431138 A1 | 1/2019 |
| EP | 2486897 B1 | 5/2019 |
| KR | 20170132055 | 12/2017 |
| KR | 101841625 B1 | 5/2018 |
| WO | 2012003451 A3 | 1/2012 |
| WO | 2012003451 A3 | 4/2014 |
| WO | 2016116397 A1 | 7/2016 |
| WO | 2018057667 A1 | 3/2018 |
| WO | 2018109715 A1 | 6/2018 |
| WO | 2020174051 A1 | 9/2020 |

OTHER PUBLICATIONS

Beauchamp et al., "Dynamic Electrical Stimulation of Sites in Visual Cortex Produces Form Vision in Sighted and Blind Humans," bioRxiv preprint, http://dx.doi.org/10.1101/462697, Nov. 5, 2018, 24 pgs.

Lee et al., "Engineering Artificial Somatosensation Through Cortical Stimulation in Humans," Frontiers in Systems Neuroscience, www.frontiersin.org, Jun. 4, 2018, vol. 12, Article 24, 11 pgs.

Roelfsema et al., "Mind Reading and Writing: The Future of Neurotechnology," Trends in Cognitive Sciences, https://doi.org/10.1016/j.tics.2018.04.001, May 6, 2018, Elsevier Ltd., 14 pgs.

Anderson et al., "Optimized Programming Algorithm for Cylindrical and Directional Deep Brain Stimulation Electrodes," https://doi.org/10.1088/1741-2552/aaa14b, Journal of Neural Engineering, Jan. 24, 2018, IOP Publishing Ltd., 19 pgs.

"Swan et al., ""Sensory Percepts Induced by Microwire Array and DBS Microstimulation in Human Sensory Thalamus,"" https://doi.org/10.1016/j.brs.2017 .10.017, Brain Stimulation 11 (2018) 416-422, Elsevier Inc."

Yadav, A.P., Li, D. & Nicolelis, M.A.L.: "A Brain to Spine Interface for Transferring Artificial Sensory Information". Sci Rep 10, 900 (2020),15 pgs.

"Sensory Electrical Stimulation Cueing May Reduce Freezingof Gait Episodes in Parkinson's Disease"; L. Rosenthal et. al.; Hindawi Journal of Healthcare Engineering; 2018, Article ID 4684925, 6 pgs.

"Effect of rhythmic auditory cueingon parkinsonian gait: A systematic review and meta-analysis"; S. Ghai et al.; Nature Scientic Reports; (2018) 8:506; DOI:10.1038/s41598-017-16232-5, 19 pgs.

Examination Report for German Application No. 1020192014752.6, dated Apr. 16, 2021, 5 pgs.

Examination Report for German Application No. 1020192014752.6, dated Jun. 16, 2020, 8 pgs.

Invitation to Pay Additional Fees and, Where Applicable, Protest Fee and Partial International Search for PCT/EP2020/055156, dated May 29, 2020, 21 pgs.

Heming E A et al: "Designing a Thalamic Somatosensory Neural Prosthesis: Consistency and Persistence of Percepts Evoked by Electrical Stimulation", IEEE Transactions on Neural Systems and Rehabilitationengineering, IEEE Service Center, New York, NY, US, vol. 19, No. 5, Oct. 1, 2011 (Oct. 1, 2011), pp. 477-482.

Donati, A., Shokur, S., Morya, E. et al. "Long-Term Training with a Brain-Machine Interface-Based Gait Protocol Induces Partial Neurological Recovery in Paraplegic Patients" Sci Rep 6, 30383 (2016); https://doi.org/10.1038/srep30383, 16 pgs.

First Office Action dated Mar. 17, 2020 for German Application No. DE102019209096.6, 8 pages.

Heming E., et al., "Designing a Somatosensory Neural Prosthesis: Percepts Evoked by Different Patterns of Thalamic Stimulation," Journal of Neural Engineering, Dec. 1, 2010, vol. 7 (6), 7 pages.

International Preliminary Report issued in International Application No. PCT/EP2020/055156, dated Sep. 10, 2021, 17 pages.

International Search report and Written Opinion issued in International Application No. PCT/EP2020/055156, dated Jul. 21, 2020, 22 pages.

Office Action for European Application No. 20200707624, dated Dec. 7, 2021, 14 pages.

* cited by examiner

CLOSED LOOP COMPUTER-BRAIN INTERFACE DEVICE

This application claims priority to German Patent Application Number 10 2020 210 676.2 titled "Closed Loop Computer-Brain Interface Device" and filed on Aug. 21, 2020, which is hereby incorporated by reference in its entirety, as though fully and completely set forth here.

1. TECHNICAL FIELD

The present invention relates to closed loop computer brain interface devices, systems and computer programs that may be used for behavioral task training as well as patient recovery and rehabilitation.

2. TECHNICAL BACKGROUND

Movement disorders and unsafe, undesirable or unstable movements can originate from a range of medical conditions such as traumatic brain injury, stroke, cerebral palsy, Parkinson's disease (PD) and Parkinsonism, dystonia, Huntington's disease, ataxia, the many varieties of tremor, myoclonus, tics, Tourette's syndrome, restless leg syndrome, gait disorders, balance disorders, and the like.

For instance, in the United States, it is estimated that over 270,000 individuals are hospitalized each year for a traumatic brain injury and survive. While traumatic brain injury can result in a wide variety of cognitive impairments, motor disorders along with balance problems, are the most commonly reported symptoms. Apart from motor symptoms, many stroke survivors suffer from sensory impairments of their affected upper limbs which are characterized by reduced sense of touch, temperature, proprioception, and pain. These symptoms can affect the ability to use the upper limbs in everyday activities.

There is consistent clinical evidence that somatosensory dysfunction negatively influences motor function. The impairments affect the ability to discriminate textures, weights, shapes, and sizes, to grasp and manipulate objects without vision, and to perform tasks using hands in everyday life. However very little attention is paid to sensory impairments in rehabilitation and recovery and behavioral task training.

For instance, conventional rehabilitation commonly involves a series of motor or cognitive tasks performed by a patient in context of physical therapy delivered by human therapists. More recently, robotic rehabilitation systems have been described that complement human therapists and enable novel rehabilitation exercises which may not be available from human therapists alone. For instance, a rehabilitation robot such as the BURT (cf. https://medical.barrett.com) can provide active visual, auditory, proprioceptive, and vibration feedback associated with a behavioral training task.

Further, the publication Donati, A., Shokur, S., Morya, E. et al. "*Long-Term Training with a Brain-Machine Interface-Based Gait Protocol Induces Partial Neurological Recovery in Paraplegic Patients*" Sci Rep 6, 30383 (2016); https://doi.org/10.1038/srep30383 suggests the importance of tactile feedback in long-term rehabilitation. The study demonstrates that long-term exposure to brain computer interface (BCI)—based protocols enriched with tactile feedback and combined with robotic gait training may induce cortical and subcortical plasticity capable of triggering partial neurological recovery even in patients originally diagnosed with a chronic complete spinal cord injury.

US 2010/0057161 A1 relates to treating medical conditions such as unilateral motor deficits, movement disorders, psychiatric disorders, epilepsy, speech or cognitive deficits associated with hemispheric lesions by neuromodulation. Further, US 2010/0057161 A1 also discloses a method for enhancing memory, learning and/or cognitive capacity in a healthy individual by stimulating a target site of a cerebello-thalamo-cortical pathway and/or a cortical-ponto-cerebellar pathway.

US 2015/0073492 relates to systems for treating motor deficits in stroke patients based on stimulating the vagus nerve of the patients during the performance of a selected therapeutic tasks, and thereby improving the patient's motor deficits.

U.S. Pat. No. 9,974,478 relates to an adaptive movement recovery system for providing therapy and training to improve functional motor recovery and safety of movement of a subject suffering from an injury or from movement disorders.

U.S. Pat. No. 8,509,904 relates to a BCI apparatus for supporting the rehabilitation of stroke patients with motor impairments. The disclosed apparatus comprises an electrocorticography (EcoG) multi-electrode probe for recording neuronal activity signals, an evaluation unit for analysis of the activity signals, and an effector which is controlled by the evaluation unit in dependence of a detected motion. The effector can be an orthosis, or a display device or other effector means such as a stimulator for muscle or brain tissue, which gives the patient feedback about the degree of success of control.

EP 2 486 897 B1 relates to an interface between a machine and a patient's brain, and more particularly to an interface between one or more types of neural signals originating in the brain of a patient. The neural signals are monitored and transmitted to a responsive mechanical device, which, in turn, relays sensory feedback to the patient. In this manner, one or more neural signals originating in a subject's brain are converted to motion in a mechanical device.

WO 2012/003451 A3 relates to a closed-loop electrical stimulation system comprising an electrode assembly adapted to electrically stimulate signal to the nervous system or muscles of a user, a sensor system adapted to detect a mechanical response to a muscle stimulation signal of a muscle associated with a muscle group stimulated by the nervous system and an electrical stimulation device operably coupled to the electrode assembly and the sensor system that includes a control system to receive feedback from the muscle and to adjust a parameter of the muscle stimulation signal as well as a programmed microprocessor for receiving input from the sensor system and controlling the electrical stimulation.

US 2014/0379046 A1 relates to an implantable neurostimulator system for treating movement disorders that includes a sensor, a detection subsystem capable of identifying episodes of a movement disorder by analyzing a signal received from the sensor, and a therapy subsystem capable of supplying therapeutic electrical stimulation to treat the movement disorder. The system treats movement disorders by detecting physiological conditions characteristic of an episode of symptoms of the movement disorder and selectively initiating therapy when such conditions are detected.

Similarly, U.S. Pat. No. 8,423,145 B2 relates to an implantable neurostimulator system adapted to provide therapy for various neurological disorders that is capable of varying therapy delivery strategies based on the context, physiological or otherwise, into which the therapy is to be delivered. Responsive and scheduled therapies can be varied depending on various sensor measurements, calculations, inferences, and device states to deliver an appropriate therapy.

Further information on the technical background of the present invention is provided by prior art documents U.S. Pat. Nos. 8,290,596, 8,475,172, 9,357,938, EP 2 552 304, US 2015/0018724.

The prior art systems and devices discussed above exhibit various deficiencies.

For instance, several of the discussed prior art systems require implantation of dedicated interface devices such as dedicated cortex stimulation electrodes via invasive surgical procedures that may not be safe and/or not yet fully approved for widespread clinical use. Moreover, the available systems for aiding patients during rehabilitation from neurological diseases or injury rely on unspecific or indirect feedback resulting in an unsatisfactory therapy success. In addition, many of the prior art systems cannot be calibrated for individual patients and thus lack the capability to perform patient specific therapy optimization.

Moreover, some of the prior art systems such as the brain-machine interface disclosed in EP 2486897 B1 use sensory feedback to improve control of a mechanical device via the brain-machine interface. However, such systems are fundamentally limited to sensory feedback mimicking the bioelectric signals normally generated from physiological sensory organs (e.g. visual feedback signals obtained from a retina implant, auditory feedback signals obtained from a cochlea implant etc.). Naturally, such plain sensory feedback is thus limited to physiological sensory modalities.

It is thus a problem underlying the present invention to overcome such deficiencies of previous technologies by providing novel neuronal stimulation equipment that may be used for treating or rehabilitating cognitive and/or motor deficits due to neurological disorders or injury. The present invention is further directed to provide novel behavioral training paradigms and devices that are based on neurostimulation techniques.

3. SUMMARY OF THE INVENTION

The above-mentioned problems are at least partially solved by a closed loop CBI (CLCBI) device as specified in independent claim 1 and by the computer program of independent claim 17. Exemplary embodiments of the present invention are specified in the dependent claims.

Generally, the present invention allows to implement a novel closed-loop approach to patient rehabilitation and recovery as well as sensory enhancement and behavioral task training. This approach is based on direct neurostimulation of afferent sensory axons (e.g. thalamoctical axons and/or afferent sensory axons of the spinal cord) targeting directly or indirectly (i.e. via multi-synaptic afferent pathways of the central nervous system) specific sensory neurons in the cortex to support an individual with executing a behavioral task while taking into account task performance and/or a behavioral or movement state of the patient via a feedback loop, for purposes including enhanced motor, sensory and cognitive learning and/or memory formation. For instance, the present invention is well suited to reinforce active daily living tasks (ADL) in patients recovering from post-stroke symptom. A simple instance of such a behavioral task may include a reach and grasp task where selective neurostimulation provided at pitch moments during the task can provide sensory cues associated with task training indications to the individual in the same manner as a human therapist assisting the individual to better learn the task.

More specifically, the present invention provides a CLCBI device for an individual comprising a receiver module configured to obtain at least one sensor signal indicative of a movement or action of the individual, a processing module operably connected to the receiver module and configured to determine at least one neuronal feedback signal based at least in part on the obtained sensor signal and a transmitter module operably connected to the processing module and configured to transmit the determined neuronal feedback signal to a neurostimulation device of the individual or a neurostimulation module operably connected to the processing module, wherein the neuronal feedback signal is configured to elicit a sensory percept in the cortex of the individual via stimulating afferent sensory axons of the central nervous system targeting sensory neurons of the cortex, and wherein the elicited sensory percept indicates movement support information related to the obtained sensor signal to support the execution of the movement or action of the individual.

The various modules of the devices and systems disclosed herein can for instance be implemented in hardware, software or a combination thereof. For instance, the various modules of the devices and systems disclosed herein may be implemented via application specific hardware components such as application specific integrated circuits, ASICs, and/or field programmable gate arrays, FPGAs, and/or similar components and/or application specific software modules being executed on multi-purpose data and signal processing equipment such as CPUs, DSPs and/or systems on a chip (SOCs) or similar components or any combination thereof.

For instance the various modules of the CLCBI device discussed above may be implemented on a multi-purpose data and signal processing device configured for executing application specific software modules and for communicating with various sensor devices and/or neurostimulation devices via conventional wireless communication interfaces such as a NFC, a WIFI and/or a Bluetooth interface.

Alternatively, the various modules of the CLCBI device discussed above may also be part of an integrated neurostimulation apparatus, further comprising specialized electronic circuitry (e.g. neurostimulation signal generators, amplifiers etc.) for generating and applying the determined neuronal feedback signals to a neurostimulation interface of the individual (e.g. a multi-contact deep brain stimulation (DBS) electrode, a spinal cord stimulation electrode, etc.).

The neuronal feedback signals generated by the CLCBI device described above may for instance also be transmitted to a neuronal stimulation device comprising a signal amplifier driving a multi-contact DBS electrode that may already be implanted into a to patient's brain for a purpose different than providing the neuronal feedback signals or to a spinal cord stimulation interface. Alternatively, dedicated DBS-like electrodes or spinal cord stimulation electrodes may be implanted for the purpose of applying the neuronal feedback signals generated by the CLCBI device via established and approved surgical procedures that were developed for implantation of conventional DBS electrodes or spinal cord stimulation electrodes. Further, as mentioned above the CLCBI device described above may also be integrated together with a neuronal stimulation device into a single device.

Further, it is important to note that the movement support information that is indicated by the sensory percept elicited by the neuronal feedback signal differs from mere sensory feedback. As will be explained in detail below (see for example FIG. 6 and FIG. 11a/b) any kind of abstract information that can support the execution of the movement or action (e.g. a geographic position indication, a distance indication, a movement trajectory indication etc.) can be transmitted to the individual with a CLCBI device according to the present invention. For instance, different neuronal feedback signals may be configured to elicit sensory percepts related to a specific sensation (e.g. a tough sensation in the left hand) having different characteristics (e.g. different intensities or frequencies). The CLCBI device provided by the present invention may then be calibrated such that the different characteristics of the elicited sensory percept indicate different movement support information such as different distances to an object that is to be manipulated by the individual or a degree of deviation from a desired movement trajectory that is to be executed by the individual.

For instance, the action or movement executed by the individual and supported by the CLCBI device may be associated with a training task and the movement support information may support the individual with performing the training task.

In particular, the movement support information provided by the neuronal feedback signal may be configured to provide one or more of the following to the individual: a distance indication relating to an object to be manipulated by the individual, an orientation indication for the individual or a body part of the individual, a success or failure indication for a training task executed by the individual, an indication, preferably continuous, of a desired or unwanted trajectory of a movement or action to be executed by the individual, an indication quantifying a degree of deviation from a desired trajectory of a movement or action to be executed by the individual, an indication designating a desired or unwanted object to be manipulated by the individual, an indication to start of stop the execution of the movement or action and an indication configured to provide the individual with a non-verbal instruction related to the execution of a task.

The present invention also provides a computer program comprising instructions for carrying out the following steps when being executed by the signal processing and transceiver modules of a signal and data processing device, a neuronal stimulation device or system: obtain at least one sensor signal indicative of a movement or action of an individual, determine a neuronal feedback signal based at least in part on the obtained sensor signal, and transmit the neuronal feedback signal to a neurostimulation device or module of the individual, wherein the neuronal feedback signal is configured to elicit a sensory percept in the cortex of the individual via stimulating afferent sensory axons of the central nervous system targeting sensory neurons of the cortex, and wherein the elicited sensory percept indicates artificial movement support information related to the obtained sensor signal to support the execution of the movement or action of the individual.

Further, the at least one sensor signal that is obtained by the CLCBI device may be indicative of at least one of the following:
  a position, distance, and/or orientation of a body part of the individual with respect to a fixed reference frame and/or another body part of the individual, and/or an object to be manipulated by the individual;
  a muscle tension, contraction and/or relaxation state of the at least one body part of the individual;
  a flexion, extension, supination, pronation and/or rotation angle of a joint of the at least one body part of the individual;
  a movement speed or acceleration associated with the at least one body part;
  a contact pressure between a portion of the at least one body part and an object to be manipulated by the individual.

In this way the CLCBI device is enabled to obtain and take into account detailed information about the state of the body of the individual that is operating the CLCBI device (e.g. while performing a behavioral learning/training task or a rehabilitation and recovery procedure) and thus is enabled to determine and transmit highly specific neuronal feedback signals that facilitate faster and more task specific learning success. As mentioned above the neuronal feedback signal may be determined based on processed input data from multiple signal sources such as video cameras and force, acceleration and/or position sensors, or biopotential transducers. The processed feedback information may be utilized to trigger neurostimulation by activating appropriate perceptual/sensory communication channels. In this manner, the present invention allows the use accurately timed message blocks that provide effective and automatic sensory feedback cues to the individual to enhance and fine-tune performance on behavioral tasks.

For instance, the obtained sensor signals may be received from at least one of the following sensor devices: a computer vision tracking device; a kinematic sensor device; a touch sensor; a force, angle, position, tension and/or acceleration sensor device; an electroencephalography device; an electromyography device; a skin conductance, respiratory rate, electrocardiogram, and temperature sensor device, a deep brain local field potential recording device; and an electrocorticography device.

The receiver module of the CLCBI device may further be configured to obtain training data indicative of a training task associated with the movement or action of the individual.

For instance, the movement support information may indicate to the CLCBI device that a desired behavioral task was completed successfully or partially successfully or that the task has failed. Other movement support information might provide information about a desired movement trajectory to be executed during training. In response, the CLCBI device may generate a neuronal feedback signal that is transmitted to a neuronal stimulation device of the individual (e.g. a neurostimulation signal generator and amplifier driving one or more contacts of a DBS electrode or a spinal cord stimulation electrode), wherein the neuronal feedback signal is configured such that a sensory percept is elicited in the cortex of the individual corresponding to the desired movement support information, e.g. providing the desired training indication as discussed above.

Further, the CLCBI device described above may be further configured to access a data storage device storing a plurality of relations, specific for the individual, associating a plurality of neuronal feedback signals with a plurality of corresponding movement support information. In some embodiments, the CLCBI device may also include the data storage device storing the plurality of relations, specific for the individual, associating the plurality of neuronal feedback signals with the plurality of corresponding movement support information.

For instance, the data storage device may contain a personalized communication library for the individual, the library storing the relations between a plurality of movement support information and a plurality of corresponding neuronal feedback signals. Such a stimulation/feedback signal library can be calibrated for each individual through neuroimaging and/or individualized testing of the individual. Neuroimaging may first be used to identify theoretically possible ranges of activation for an individual stimulation electrode while individualized testing determines which points in the parameter space of feedback signal parameters can be perceived and decoded by the cortex of the individual. It should be emphasized that conscious individualized testing of an individual is merely one specific example of how to generate the individualized relations stored in the memory. In other embodiments such relations may also be obtained from unconscious patients, e.g. through the non-invasive observation of corresponding functional MRI responses on the somatosensory cortex or EEG recordings.

Further, once the communication library is established or while it is being established for an individual a specific training procedure can be executed that links a specific sensory percept to the corresponding movement support information. As long as the cortex of the individual responds to classical conditioning, pair learning can be executed. In the context of the present invention, such a pair consists of a given sensory percept corresponding to a given neuronal feedback signal and the corresponding movement support information (e.g. an indication related to execution of a behavioral training task/procedure as discussed above) to be associated with said given sensory percept and the corresponding neuronal feedback signal.

Importantly, the type of information to be conveyed via the CLCBI device described above whether it is a movement support information or similar information can be chosen more or less freely. Any information or message which can be broken down into message blocks (i.e. pieces of conceptual information that can be decoded by the cortex of an individual) can be transmitted. This includes continuous neuronal feedback signals such as a (quasi-) continuous indication of a desired movement trajectory or other information that may be relevant for executing the desired movement or action (e.g. a start or stop indication, an indication of objects to be avoided or manipulated, etc.).

In particular, the specific relations may be based at least in part on one or more of the following: conceptual or perceptual learning data for the individual, neuro-imaging data for the individual, electrophysiological measurement data for the individual, neuronal connectivity information for the individual, electric field simulation data for the neurostimulation device of the individual and neuronal excitability model data for the individual.

In this way, even complex movement support information such as a continuous movement trajectory indication can be associated with corresponding sensory percepts that are specific for each individual. For instance, the individual may participate in a conceptual learning procedure in order to establish a perceptual communication channel (PC) for communicating artificial sensory input signals provided from a motion tracking camera system or similar sensor equipment.

Further, the neuronal feedback signal may be characterized by a plurality of signal parameters such as a signal waveform, a signal frequency, a signal polarity, a signal pulse shape, a signal amplitude and/or a signal pulse width and wherein different combinations of signal parameters correspond to different movement support information.

Moreover, the neuronal feedback signal may be adapted to elicit a sensory percept in a portion of the cortex of the individual that is associated with a specific sensory modality and wherein the portion of the cortex is one or more of the following: a somatosensory cortex area; an auditory cortex area; a visual cortex area; an olfactory cortex area; an entorhinal cortex area or components of the circuit of Papez.

In particular, the neuronal feedback signal may be configured to stimulate thalamocortical axons projecting from the thalamus to the sensory neurons of the cortex. For instance, if the neuronal feedback signal is to be applied via a conventional DBS electrode the signal parameters of the neuronal feedback signal may be adjusted such that action potentials are elicited in specific sub-populations of such thalamocortical axons, e.g. in a set of axons projecting to specific somatosensory neurons in the cortex. Alternatively or additionally, the neuronal feedback signal may also be configured to stimulate afferent sensory axons of the spinal cord projecting directly (i.e. via a monosynaptic pathway) or indirectly (i.e. via a multi-synaptic pathway) to the thalamus or the cortex.

In general, the sensational modality, location, type, and intensity of the sensory percept that is elicited in the cortex in response to these afferent action potentials can be controlled via precise electrode location and selection of neurostimulation parameters. The present invention uses such artificial sensations to transmit information directly to the brain in form of discrete or continuous message blocks by forming the desired PCs. As discussed above the PCs may be established via a single or via multiple electrical contacts of a DBS electrode or a spinal cord stimulation electrode which are electrically activated with calibrated neurostimulation parameters to deliver specific sensory messages to the individual. The sensation modality of the mentioned PCs may include tactile, proprioceptive, visual, or auditory sensations based on the application or location and orientation of the implanted stimulation electrode.

Furthermore, various biological signals, including kinematic data (accelerometer) and those obtained using electromyography (EMG), EEG, ECoG, and local field potentials, (LFPs), could also be considered as sensor input signals that may be used by the CLCBI device to determine corresponding neuronal feedback signals. Each of these feedback modalities varies with respect to invasiveness, resolution, signal content, and clinical relevance. For instance, data from accelerometers can detect onset of the movement or alternatively detect symptoms such as tremor. Surface EMG (sEMG) from symptomatic limbs or muscle groups can provide useful information as a biomarker for example to initiate stimulation in a movement-triggered fashion.

In a further embodiment, the present invention provides a recovery and rehabilitation system comprising the above discussed CLCBI device. For instance, such a recovery and rehabilitation system may in addition to the CLCBI device also comprise at least one of the above described sensor devices and/or the above described data storage device and/or a neuronal stimulation device and/or a corresponding neurostimulation electrode. Several or all of these system components may also be integrated in a single integrated multi-purpose neuronal stimulation device.

Further, the above discussed CLCBI device may also be used in a prosthetic system for an individual comprising—in addition to the CLCBI device—an electromechanic prosthetic device for the individual and a control interface, device configured to control the electromechanic prosthetic device, wherein the movement support information transmitted by the CLCBI device is configured to support the control of the electromechanic prosthetic device via the control interface.

Such a prosthetic system may further comprise at least one of the sensor devices and/or the data storage device described in detail above.

Moreover, the control interface device of such a prosthetic system may comprise a brain computer interface device, BCI, configured to monitor neural activity of the individual related to the control of the electromechanic prosthetic device.

In this way the present invention even facilitates the design of novel closed loop artificial body parts.

4. SHORT DESCRIPTION OF THE FIGURES

Figure 2:
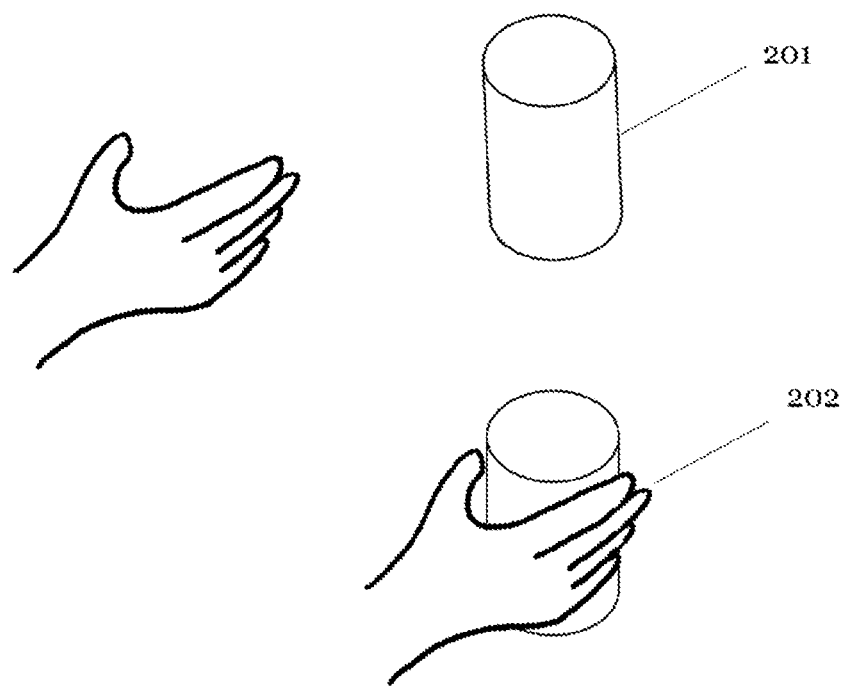
Figure 3:
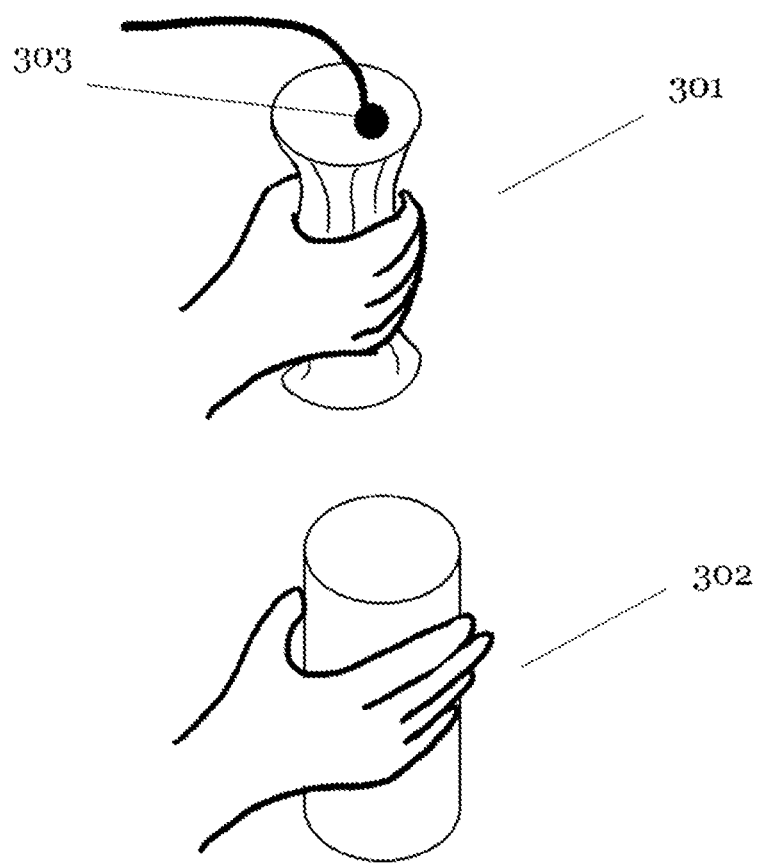
Figure 4:
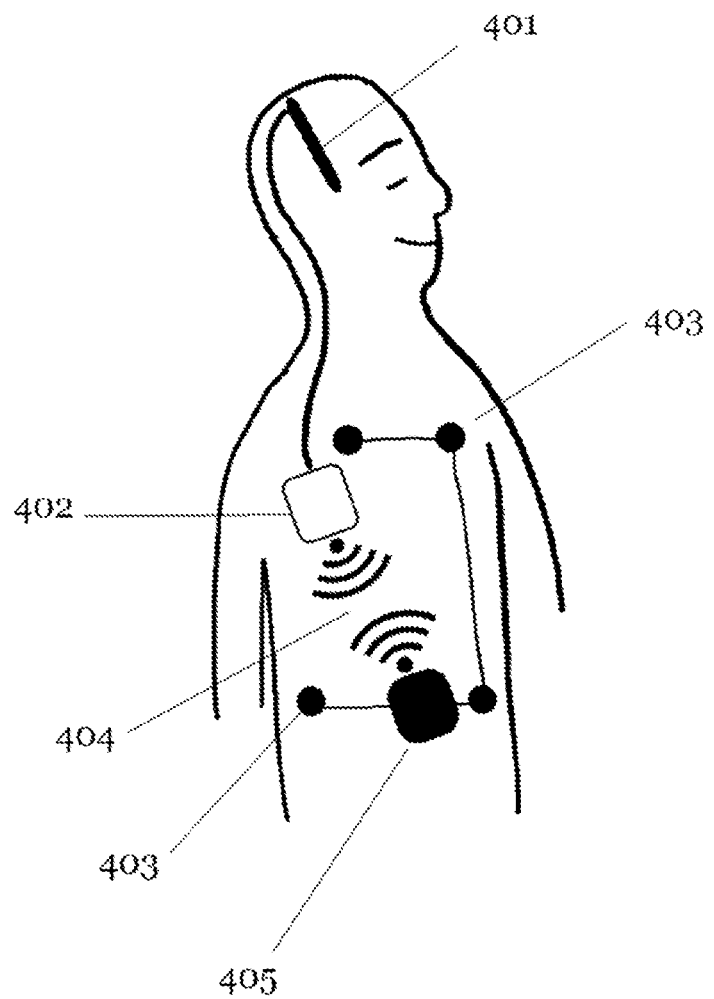
Figure 5:
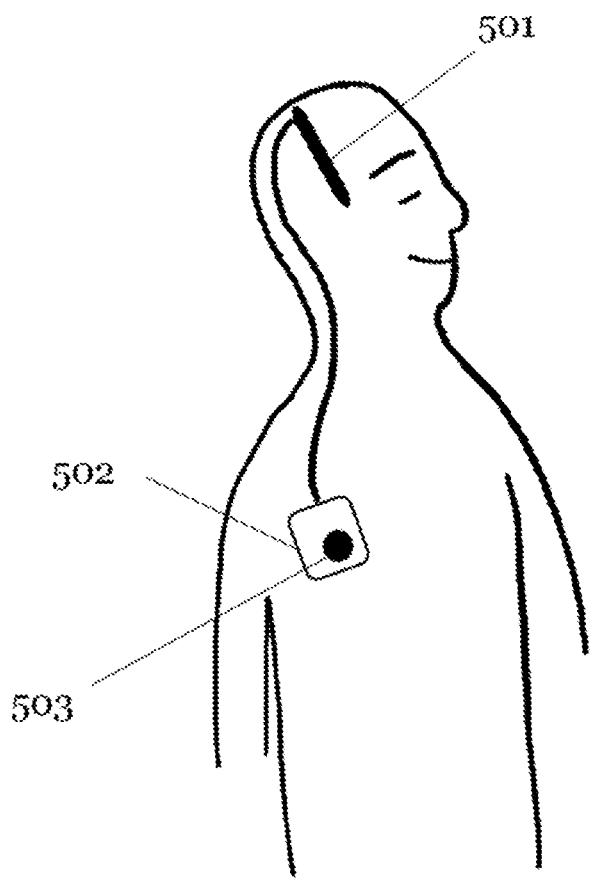
Figure 6:
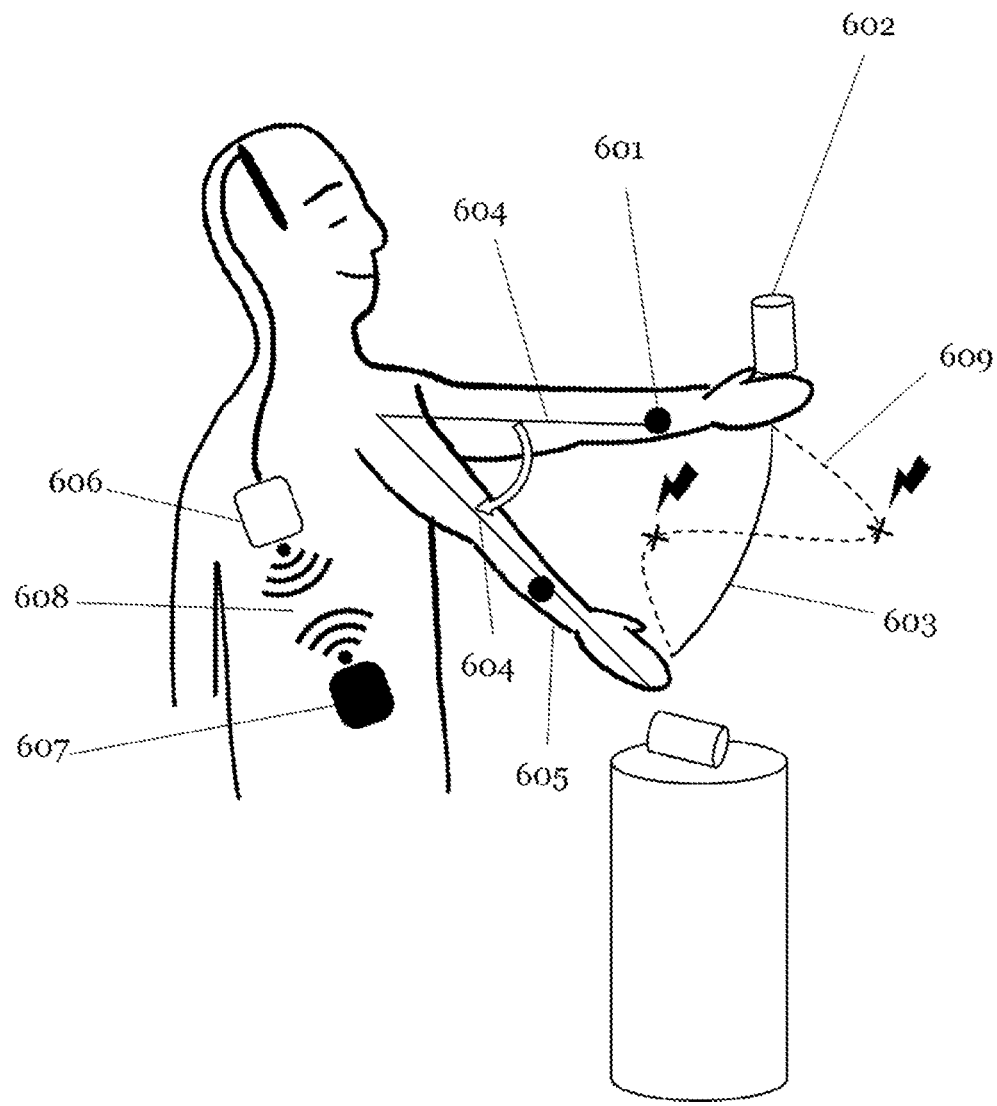
Figure 7:
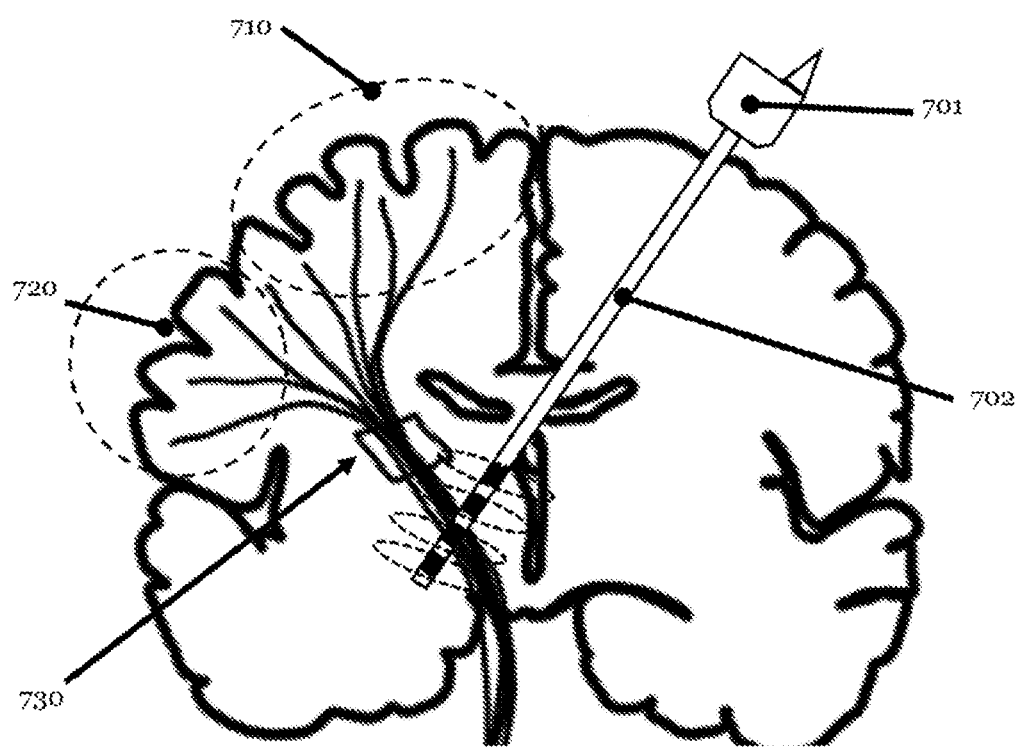
Figure 8:
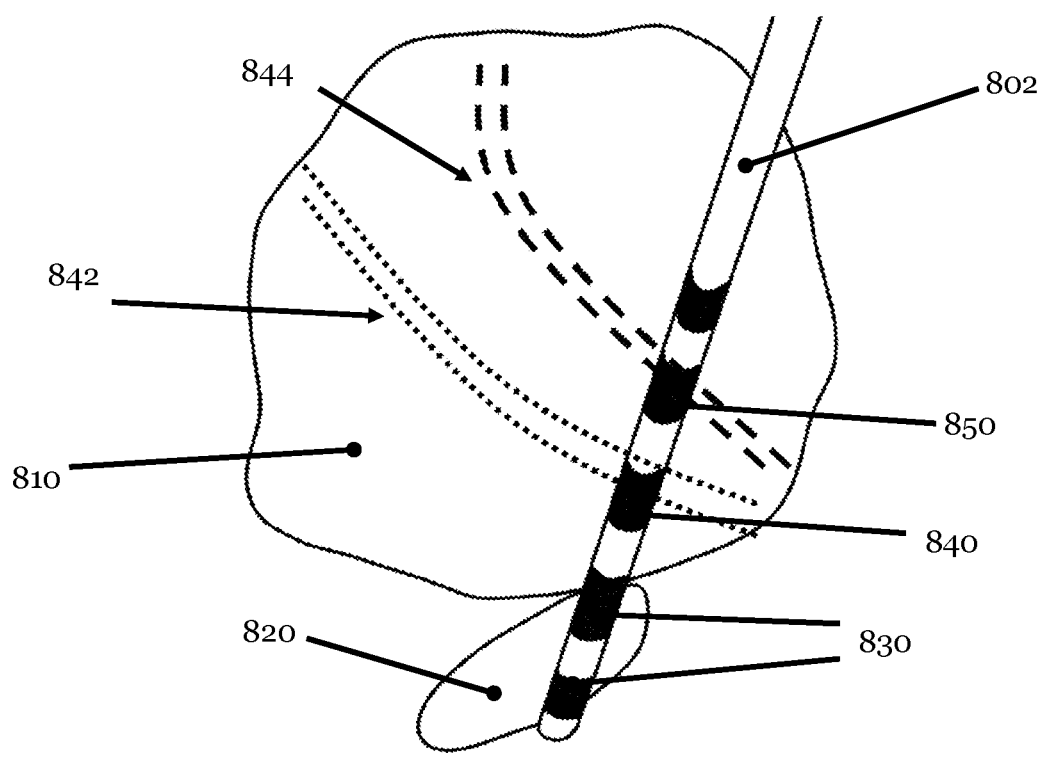

Various aspects of the present invention are described in more detail in the following by reference to the accompanying figures. These figures show:

FIG. 1 a diagram illustrating an individual taking part in a behavioral training task such as a recovery and rehabilitation procedure using a CLCBI device according to an embodiment of the present invention;

FIG. 2 a diagram illustrating a movement or action of an individual that may be supported by movement support information generated by a CLCBI device according to an embodiment of the present invention;

FIG. 3 a diagram illustrating a force sensor generating a sensor signal that may be used as input to a CLCBI device according to an embodiment of the present;

FIG. 4 a diagram illustrating the design of a closed loop balance rehabilitation system using an array of accelerometers in conjunction with a CLCBI device according to an embodiment of the present invention;

FIG. 5 a diagram illustrating the design of a closed-loop balance rehabilitation system using accelerometers and gyroscopes integrated with a CLCBI device according to an embodiment of the present invention;

FIG. 6 a diagram illustrating the design of a (quasi-) continuous closed-loop motion correction system based on a CLCBI device according to an embodiment of the present invention;

FIG. 7 diagram illustrating a neuronal stimulation electrode for stimulating afferent axons targeting the sensory cortex of an individual. The neuronal stimulation electrode can be interfaced with a CLCBI device according to an embodiment of the present invention;

FIG. 8 a diagram illustrating a therapeutic multi-contact neuromodulation electrode. The electrode can be used for stimulating afferent axons of the central nervous system targeting the sensory cortex of an individual via a CLCBI device according to an embodiment of the present invention.

Figure 9:
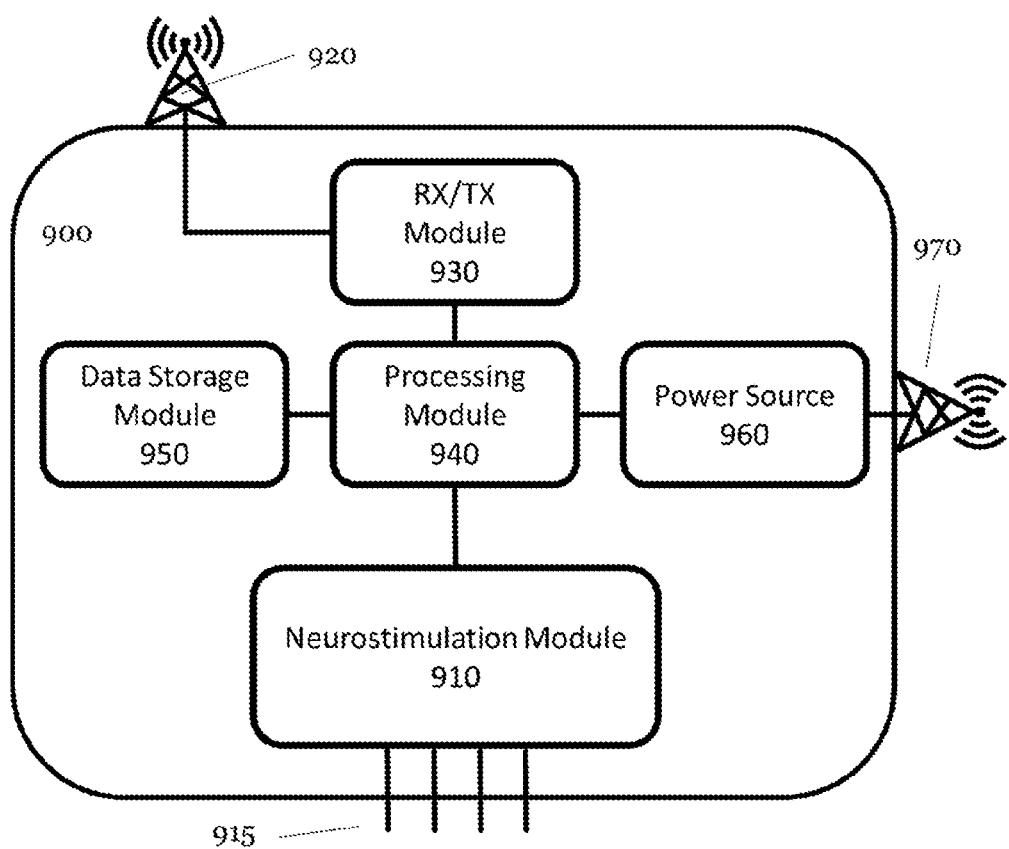
Figure 10:
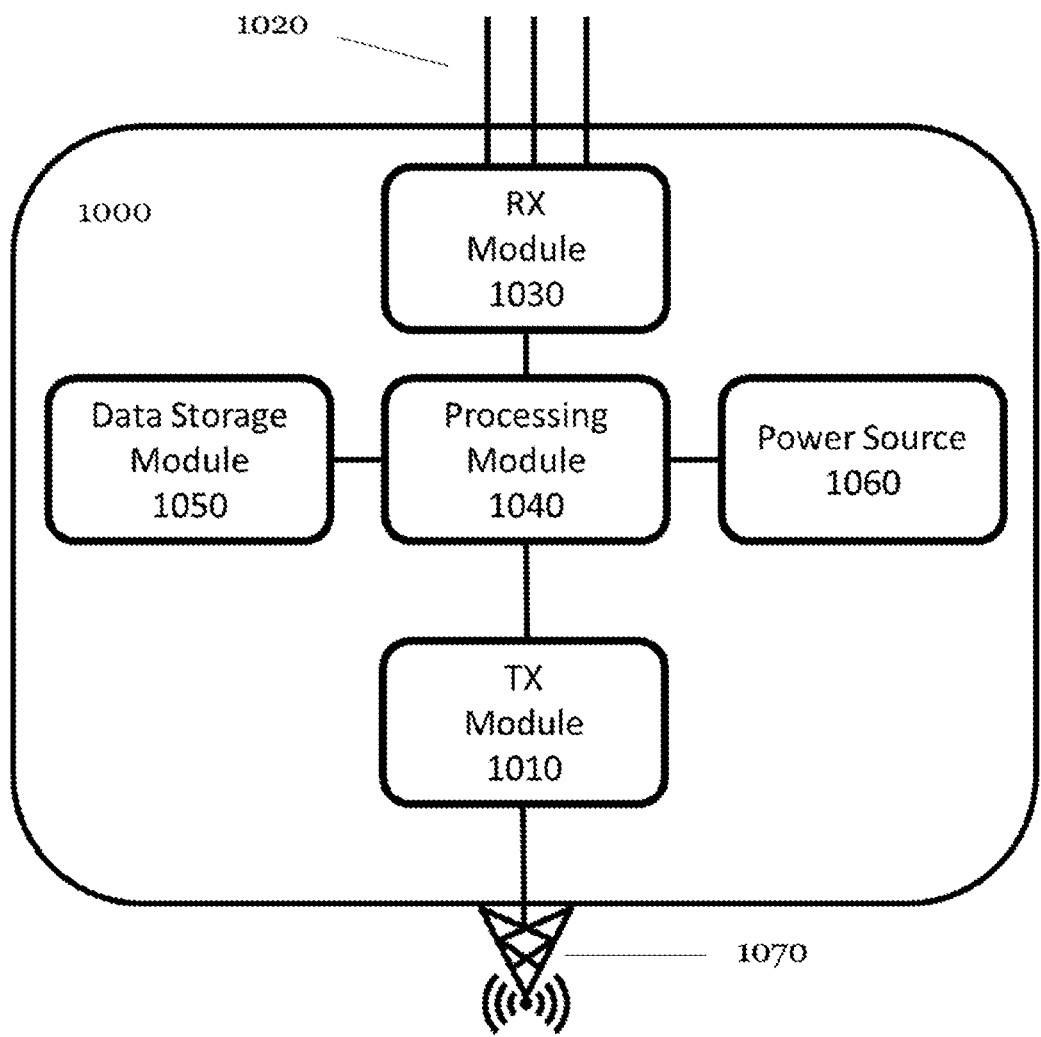
Figure 11A:
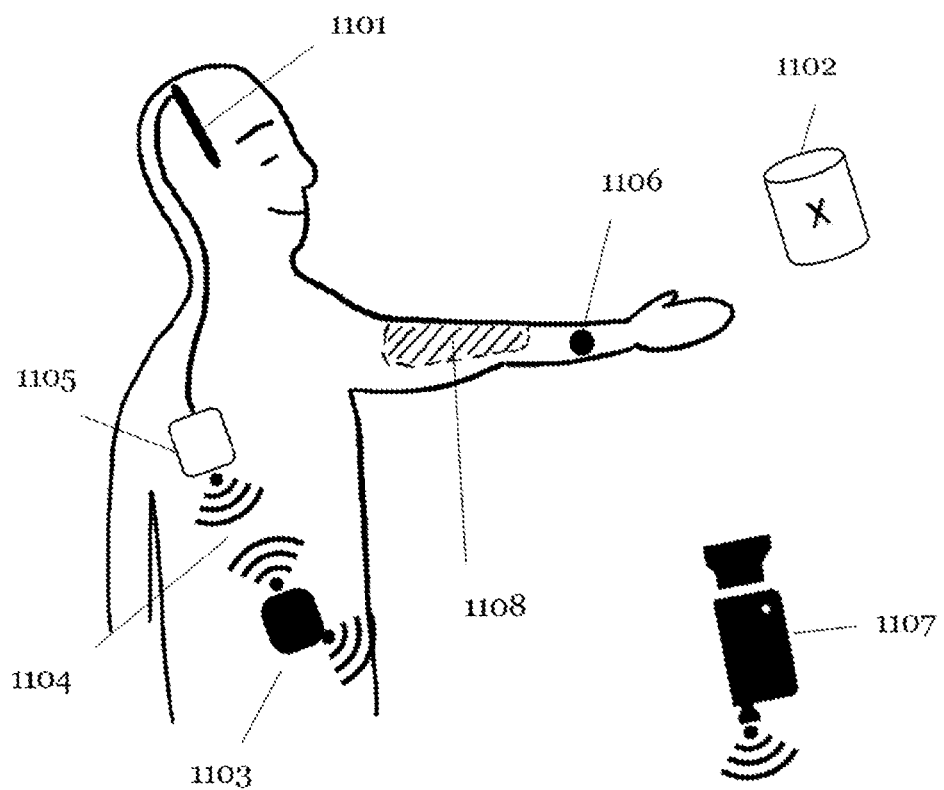

FIG. 9 a functional block circuit diagram illustrating a CLCBI device according to an embodiment of the present invention;

FIG. 10 a functional block circuit diagram illustrating a CLCBI device according to another embodiment of the present invention;

FIG. 11*a* a diagram illustrating an individual taking part in a behavioral training task using a CLCBI device according to an embodiment of the present invention; the subject is non-verbally informed to stop approaching an undesired target utilizing a specific PC established via sensory percepts associated with the arm region.

Figure 11B:
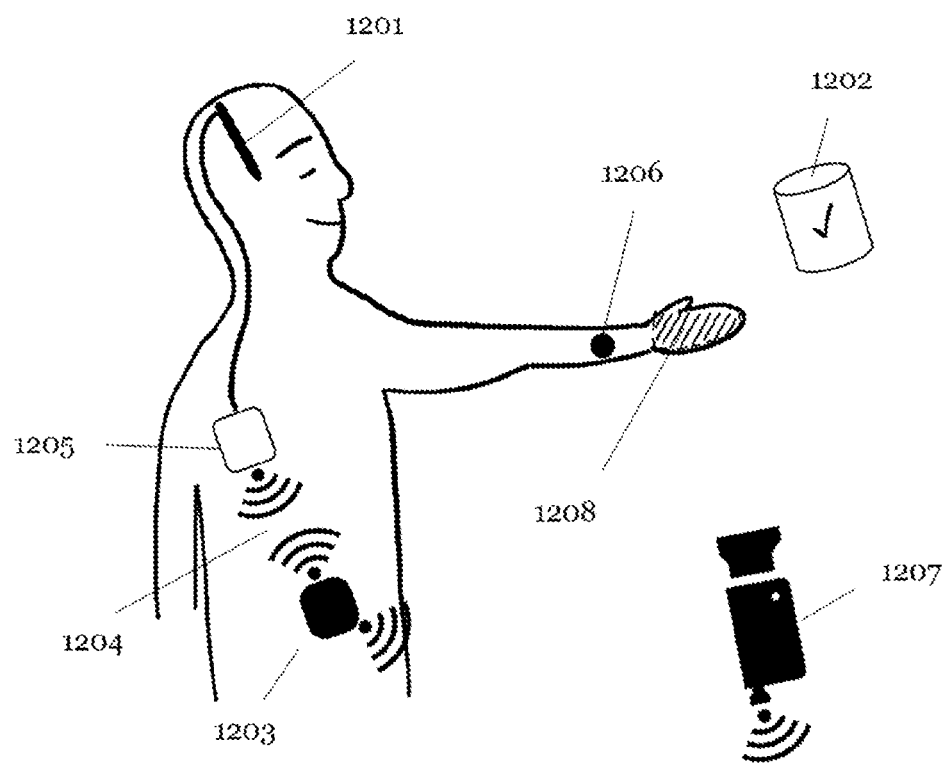

FIG. 11*b* a diagram illustrating an individual taking part in a behavioral training task using a CLCBI device according to an embodiment of the present invention; the subject is non-verbally informed to approach towards a desired target utilizing a specific PC established via sensory percepts associated with the hand area.

Figure 12:
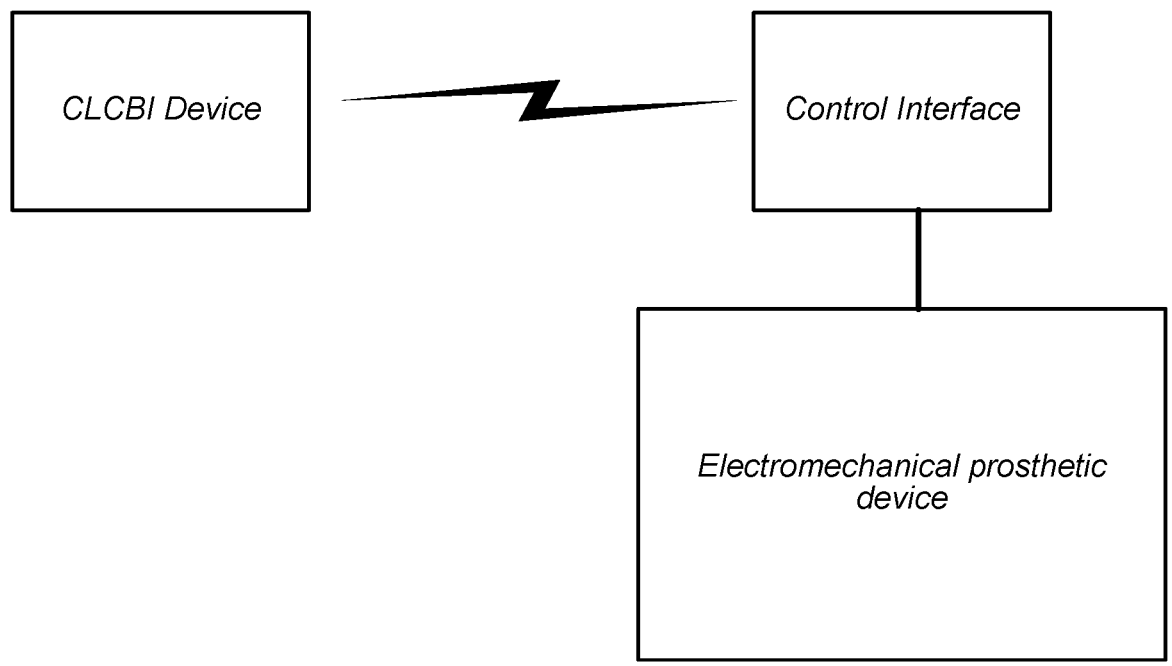

FIG. 12 a diagram illustrating a CLCBI device configured to support control of an electromechanics prosthetic device via a control interface.

5. DETAILED DESCRIPTION OF SOME EXEMPLARY EMBODIMENTS

In the following, some exemplary embodiments of the present invention are described in more detail, with reference to a CLCBI device that can be interfaced with neuronal stimulation electrodes such as DBS electrodes and/or spinal cord stimulation electrodes, e.g. via an intermediate neuronal stimulation device. However, the present invention can also be used with any other neuronal stimulation interface that is capable of stimulating afferent sensory axons of the central nervous system targeting the sensory cortex of an individual.

While specific feature combinations are described in the following with respect to the exemplary embodiments of the present invention, it is to be understood that not all features of the discussed embodiments have to be present for realizing the invention, which is defined by the subject matter of the claims. The disclosed embodiments may be modified by combining certain features of one embodiment with one or more features of another embodiment. Specifically, the skilled person will understand that features, components and/or functional elements of one embodiment can be combined with technically compatible features, components and/or functional elements of any other embodiment of the present invention.

FIG. 1 depicts an individual 100, e.g. a stroke patient, that takes part in a behavioral training task such as a rehabilitation and recovery procedure. The individual 100 has been implanted with a neuronal stimulation electrode 101 such as a DBS electrode or spinal cord stimulation electrode that may have multiple independently controllable electric contacts (see also FIG. 8). For instance, the neuronal stimulation electrode 101 may be already implanted into the brain of the individual 100 for the purpose of providing a neuromodulation therapy, e.g. for treating PD symptoms. The neuronal stimulation electrode 101 may also be implanted for other purposes such as for the purpose of neuronal communication and/or treatment of other movement impairments and neurological diseases such as Alzheimer's disease, epilepsy, depression, etc. Alternatively, the electrode 101 may also be implanted as a dedicated neurostimulation interface for the CLCBI devices provided by the present invention.

The individual 100 may be further equipped with a neurostimulation device 102, that may be an implantable and programmable pulse generator (IPG) implanted under the skin if the individual. Alternatively, the neurostimulation device 102 may be arranged on the head of the individual 100 or somewhere else on or in the vicinity of the body of the individual 100. The neurostimulation device 102 may be in wireless communication (e.g. via a Bluetooth, WI-FI, NFC or a similar wireless interface technology) with a control device/pocket processor 103, that may be implemented by a dedicated signal and data processing device such as a smartphone or a similar electronic information processing device. Depending on implementation details, the CLCBI devices provided by the present invention may be implemented via application specific hardware and/or software modules comprising circuitry and/or software instructions to implement the devices and systems according to the present invention.

The control device/pocket processor 103 may provide the individual 100 with a user interface to adjust the neuronal feedback signals and/or a neuromodulation therapy applied via the neurostimulation device 102 and the neuronal stimulation electrode 101. The control device 103 may also provide connectivity to a packet based wireless large area network such as an LTE or 5G network. For instance, the individual 100 may use the control device 103 to adjust signal parameters such as a signal frequency, a pulse width, a pulse shape and/or a signal amplitude of the neuronal feedback signals as well as for retrieving data from the internet.

The various modules of the CLCBI device provided by the present invention may be implemented by the control device 103, the neuronal stimulation device 102 or by a combination thereof (for examples see FIGS. 9 and 10).

The CLCBI device provided by the present invention can for instance assist patients that are rehabilitating from sensory-motor deficits due to acute or chronic neurological disease such as stroke via performing repetitive goal-directed sensory-motor tasks, as depicted in FIG. 1. During the rehabilitation procedure, the patient is instructed to perform a therapeutic task such as reaching and grasping for an object 108. The reaching motion could be defined in such a way that it incorporates specific muscle groups that require rehabilitation.

The communication channels established by the CLCBI device may be utilized in different ways including but not limited to cueing the patient at an exact moment in time to provide artificial sensory feedback cues to the patient. The cueing information may include physical requirements of correct task performance such as ideal hand position, joint angles, adequate force to hold an object, or information about shape or texture of objects.

Information such as sEMG muscle activity 105, accelerometer or gyroscope data 106, as well as the outputs of a motion tracking system 107 may be input into the pocket processor/control device 103. The pocket processor/control device 103 may be responsible for performing preprocessing on raw input information to remove noise and artifacts. Afterwards, the input data may be further analyzed by the pocket processor/control device 103 in order to determine at which point in time what type of stimulation program needs to be activated by the IPG 102. Each message block may therefore include a series of stimulation programs which may be preloaded in the IPG during a calibration phase. Once data processing is finalized on the pocket processor 103, it may transmit trigger information along with a list of programs to the IPG via a wireless link 104.

In order to establish a PC, individuals may take part in an initial calibration and learning procedure where the individual too learns the interpretation of each movement support information through an initial training period. For example, activation of the first PC with medium intensity could be felt in the arm of the individual and then be assigned to a trial success indicator. Other PCs could be utilized to inform the individual too about a joint angle of the hand of the individual in a graded way such that low intensities resemble a relaxed joint and higher stimulation intensities represent a constricted or fully closed hand.

Further, the individual's limb position may continuously be tracked during task performance via a video tracking system 107 and/or via wearable accelerometers 106. The tracking data may be compared with an expected trajectory model by the pocket processor/control device 103. In case the actual limb motion is in accordance with the expected or desired trajectory, a success feedback signal is sent to the individual via the CLBIS device. This may be used to help the individual too to reinforce the correct movement and facilitate the learning and neuronal reorganization process by the brain.

Further, the movement support information could also be triggered via or based on monitoring of sEMG signals. More precisely, the individual's mobility may be restricted due to limited intensity of efferent motor signals from the brain. While these sub-threshold motor signals could not lead to limb movement, the existence of residual EMG activity can be detected and after each detection, a success message can be transmitted to the individual as neuronal feedback signal.

A PC with specific intensity level can also be used to translate timing cues to the individual. As illustrated in FIG. 2 another embodiment could involve generating timing cues to instruct the individual to open the hand as in 201 or close it again once the hand is in the correct position 202.

In another embodiment, as depicted in FIG. 3, the target object could be equipped with at least one force or touch sensor 303 providing a sensor signal corresponding to the strength of a grasping force the individual exerts of the target object when grasping it 301, 302. The force sensor 303 may also be linked to the pocket processor/control device 103 and the IPG 102 can modulate the stimulation intensity or other signal parameters of a PC based on the amount of pressure being exerted to the object.

This may be beneficial when training individuals who have lost sense of touch due to brain injuries or diseases. The CLCBI device could assist an individual performing joint angle anticipation tasks in which the individual must guess the correct joint angle in the affected limb using no visual information. The correct joint angles could be extracted in real-time mode using a computer vision system then translated into continuous stimulation patterns after being assigned to a PC. In this way, the individual can get real-time and continuous training by perceiving the joint angle via a substitute sensory modality.

The CLCBI devices provided by the present invention can be further applied to virtual reality, augmented reality, and sensory enrichment paradigms with the aim of creating a sensory-rich environment for the individual. In such applications, the individual wears goggles equipped with built-in displays then performs different tasks via interacting with objects in the virtual world using wireless joysticks. Each object may have specific properties such as texture, shape, size, or rigidity. The position of the hand-held joysticks are continuously rendered via built-in accelerometers and infrared tracking equipment. This approach may be used to provide movement support information to the individual in order to re-educate motor skills, for example, teach the individual how to reach for a target object and grasp it correctly. After the individual has accomplished the reaching task a series of separate movement support information (using other PCs) could artificially substitute a sense of touch to teach an individual to maintain a constant pressure required for holding the virtual target.

Another embodiment of the present invention includes assisting individuals, e.g. post-stroke patients, with a compromised sense of balance. For instance, the system depicted in FIG. 4 may allow an individual to maintain a correct posture and prevent falls. An array of accelerometers 403 could for instance be incorporated in a training jacket. The sensors 403 may be linked with a pocket processor/control device 405 which is in wireless communication 404 with an implanted IPG/neurostimulation device 402. The IPG 402 may be linked with at least one or ideally two (or more) implanted stimulation electrodes 401. The pocket processor/control device 405 continuously analyses the sensor signals provided from all accelerometers 403 and may be configured to detect if the body is losing balance by swaying in one direction. The pocket processor/control device 405 may then wirelessly send necessary triggers to the IPG 402 to generate movement support information for the individual to counter the body sway.

The perceived intensity of these balance cues may be proportional to the level of the body sway. Small body tilts are perceived by the subject as weak sensations while large tilts with risk of a fall are felt with larger perceived intensities.

Using bilateral DBS electrodes or bilateral spinal cord stimulation electrodes may enable the individual to experience a more naturalistic sensation with regards to the direction of the body sway such that location of the artificial perception is ipsilateral to the direction of body sway.

As shown in FIG. 5, the acceleration sensors and/or gyroscopes 503 could also be integrated inside the IPG 502 to alleviate the need for an external wearable array of accelerometers as well as wireless communication thus reducing electric power consumption while using similar implanted stimulation electrodes 501 as discussed for FIG. 4.

The CLCBI devices and system disclosed herein could also be embodied in a fashion to assist individuals to learn or master certain repetitive actions or skills by improving the safety and efficiency of their movements. For instance, the system could benefit from integrated inertia sensors to detect a state of the individual such as walking, running, or cycling. Each of the mentioned activities involve certain muscle groups which must become active sequentially at certain phases during the activity cycle. In a walking scenario, two PCs may be employed such that the individual can receive two sets of bilateral cues with different perceived intensities. Channel intensities may correspond with four different phases in the gait cycle including heel strike, early flatfoot, late flatfoot, and toe off. The same cycle may then be repeated for the other foot.

In another embodiment, the CLCBI device could be employed as a closed-loop motion corrective device as shown in FIG. 6. An example of a reach and grasp task is depicted to where an individual must reach to a target 602 then after following a specific trajectory 603 place the target 602 inside a bucket. The trajectory of the hand 605 may be determined using a wearable accelerometer 601 placed on the wrist of the individual. The accelerometer sensor 601 could also be equipped with infra-red reflective markers to enable hand motion tracking using a video camera as described above. The angle 604 of at least one joint may be calculated using the positional data with reference to the horizontal plane. For instance, the joint angle 604 calculation may be done by a wearable pocket processor/control device 607. The initial and final shoulder joint angles in the sagittal plane are also marked by the pocket processor/control device 607. Corrective movement support information could be triggered by the pocket processor/control device 607 which is in wireless communication 608 with an IPG/neurostimulation device 606 that is configured to apply neuronal feedback signals to afferent sensory axons of the central nervous system targeting the sensory cortex of the individual as explained in detail above. Various movement support information may be provided at specific points in time where the actual hand position 609 sways outside of the defined trajectory 603 (indicated by the lightning symbols in FIG. 6). The stimulation could also get triggered to correct arm position provided that the joint angle falls outside of defined range 604.

FIG. 7 depicts a neuronal stimulation electrode 702 for stimulating afferent axons 730 targeting sensory neurons in the cortex of a human brain. The afferent axons 730 that may target different sensory areas 710, 720 of the cortex that may be related to different sensory modalities (e.g. touch, temperature sense, vision, hearing, etc.) and/or different body regions (e.g. cochlea, retina, hand, tongue, foot etc.) from which the respective sensory modality is perceived by the respective area of the cortex. For instance, the cortical area 710 may be a somatosensory area of the right foot and the cortical area 720 may be a somatosensory area of the left hand.

The afferent sensory axons 730 are connected via synapses (not shown) with their respective target neurons in the respective sensory area 710, 720. For instance, the axons 730 may be thalamocortical axons relaying sensory information from the thalamus to the cerebral cortex. The neuronal stimulation electrode 720 may comprise a plurality of independently controllable electric contacts (see FIG. 8 below) that may be arranged in the vicinity of a bundle of afferent sensory axons 730 targeting the sensory areas 720 and 710 of the cerebral cortex.

In the illustrated example, the neuronal stimulation electrode 702 is connected to a neuronal stimulation device 701, which is adapted to apply neuronal stimulation signals to brain areas associated with certain neurophysiological symptoms and/or to the afferent sensory axons 730, e.g. via independently controllable electric contacts of the neuronal stimulation electrode 702. The neuronal stimulation device 701 may comprise the CLCBI device provided by the present invention or may communicate (e.g wirelessly) with the CLCBI device. In addition, the neuronal stimulation device 701 may further comprise a wireless interface for interfacing the neuronal stimulation device 701 with other devices such as the sensor devices described above or further devices that may be adapted to obtain and/or determine the waveform and/or signal parameters (e.g. pulse width, pulse shape, frequency, amplitude, number of pulses etc.) of the neuronal feedback signal that is applied by the neuronal stimulation device 701 to the afferent sensory axons 730 via the stimulation electrode 702.

For instance, the CLCBI device provided by the present invention may determine the waveform and/or signal parameters of the neuronal stimulation signal such that a desired sensory percept is elicited in a desired area of the sensory cortex of the individual. In some embodiments of the present invention, the cortex of the individual which is receiving the neuronal stimulation signal (i.e. via afferent action potentials of the stimulated afferent axons 730) may associate the corresponding sensory percept with several types of movement support information. For example, similar to learning how to understand Morse code, the individual may have previously participated in a learning procedure establishing an associative link between a given sensory percept elicited by a given neuronal stimulation signal and a corresponding movement support information that is to be communicated to the individual via the neuronal stimulation electrode 702.

In this approach no nuclei or neuron-rich grey matter are preferably targeted by the neuronal stimulation electrode 702 but preferably the axon-rich white matter of the brain or the spinal cord, which contains the information transmitting pathways the brain uses for natural neural communication of sensory information. In this manner, the present invention provides a white-matter computer-brain-interface, i.e. a device that generates and provides electrical signals the brain can interpret as meaningful sensory input, e.g. as a balance cue for countering loss of balance in recovering stroke patients.

As mentioned above the present invention is not limited to stimulating afferent sensory axons arranged within the brain. Another option, for example, is to stimulate afferent sensory axons in the spinal cord of the individual, e.g. via applying the neuronal feedback signals generated by the CLCBI device via a single or multi-contact spinal cord stimulation electrode. As long as the neuronal feedback signal is configured to elicit information carrying sensory percepts in the cortex of the individual, stimulation may be performed at various locations of the afferent sensory pathways of the central nervous system.

FIG. 8 depicts a multi-contact neuromodulation electrode 802 e.g. adapted for neuromodulation of the sub-thalamic nucleus 820 via electric contacts 830. The electrode 802 can also be used for stimulating afferent sensory axons 842, 844 projecting from the thalamus 810 to the sensory cortex of an individual via a CLCBI device according to the present invention. For example, neuronal feedback signals may be provided by unused contacts 840, 850 of the neuromodulation electrode 802 that was implanted for a therapeutic purpose (e.g. neuromodulation of the subthalamic nucleus 820 via the therapeutic electric contacts 830) different from providing the neuronal stimulation signal to the afferent sensory axons 844, 842. For instance, the contacts that are not used for neuromodulation of the sub-thalamic nucleus 820 may be used to provide different kinds of movement support information to the cortex of the individual, e.g. for supporting the individual performing a behavioral training task such as a recovery and rehabilitation procedure. For example, such movement support information may be signaled via a sensory percept elicited by a neuronal feedback signal that is applied to the axons 844 targeting a cortex area related to a touch sensation for instance in the left foot or the right hand.

In many cases, an electrode 802 that is used as a neuromodulator, e.g. for treatment of symptoms of PD etc., is not always active and/or may comprise independently controllable contacts that are not required for achieving the therapeutic purpose. Thus, the neuromodulation electrode can also be used for applying neuronal stimulation signals provided by a CLCBI device according to the present invention. For instance, if implantation in e.g. the subthalamic nucleus 820 is conducted for the tip contacts 830 to control, for example, the primary PD symptoms more distal contacts 840, 850 could be used in combination with the above disclosed invention to communicate movement support information and directly into the brain of the patient.

FIG. 9 illustrates an exemplary CLCBI device 900 according to an embodiment of the present invention. In this embodiment the CLCBI device 900 comprises an integrated neurostimulation module 910 (e.g. comprising a neuronal signal generator and an output amplifier) that is connected to a plurality of output signal leads 915 that may be interfaced with a neurostimulation interface of the individual (e.g. a DBS electrode or a spinal cord stimulation electrode). The CLCBI device 900 further comprises a communication antenna 920 operably connected to a transceiver module 930, configured for wireless communication (e.g. via NFC, Bluetooth or a similar wireless communication technology).

The transceiver module 930 is configured, for example, to receive one or more sensor signals from one or more sensors (as discussed above), indicative of an action or movement of an individual (e.g. a distance measurement obtained from a motion tracking sensor device, acceleration signals obtained form an accelerometer etc.). The transceiver module 930 is operably connected to a data/signal processing module 940 configured to generate one or more neuronal feedback signals and/or signal parameters (e.g. waveform, pulse shape, amplitude, frequency, burst count, burst duration etc.) for generating the one or more neuronal feedback signals. For instance the processing module 940 may access a data storage module 950 configured to store a plurality of relations, specific for the individual, associating a plurality of neuronal feedback signals (or parameters used for generating a plurality of neuronal feedback signals) with a plurality of corresponding movement support information.

The generated neuronal feedback signal and/or the signal parameters are input into the integrated neurostimulation module 910 that may be configured to process (e.g. modulate, switch, amplify, covert, rectify, multiplex, phase shift, etc.) the one or more neuronal feedback signals generated by the processing module 940 or to generate the one or more neuronal feedback signals based on the signal parameters provided by the processing module 940.

The generated and processed neuronal feedback signals are then output by the neurostimulation module 910 and can be applied to one or more electric contacts of a neurostimulation electrode (e.g. a DBS electrode or spinal cord stimulation electrode; not shown) via output leads 915.

The CLCBI device 900 may also comprise a rechargeable power source 960 that, for instance may be wirelessly charged via a wireless charging interface 970.

FIG. 10 illustrates a further exemplary CLCBI device moo according to an embodiment of the present invention. In this embodiment, the CLCBI device moo does not comprises an integrated neurostimulation module (see FIG. 9 above). Instead the data/signal processing module 1040 is connected to a wireless transmitter module 1010 that is connected to a wireless transmit antenna 1070. The processing module 1040 may be configured for generating one or more neuronal feedback signals and/or signal parameters (e.g. waveform, pulse shape, amplitude, frequency, burst count, burst duration etc.) for generating the one or more neuronal feedback signals. For instance the processing module 1040 may access a data storage module 1050 configured to store a plurality of relations, specific for the individual, associating a plurality of neuronal feedback signals (or parameters used for generating a plurality of neuronal feedback signals) with a plurality of corresponding movement support information.

The transmitter module 1010 is configured for wireless communication (e.g. via NFC, Bluetooth, WIFI or a similar wireless communication technology) with a neurostimulation device of the individual (not shown; see FIGS. 1, 4, 11a and 11b.). The transmitter module 1010 may be configured to transmit the generated neuronal feedback signal and/or the generated feedback signal parameters to the neurostimulation device of the individual that may be configured to process (e.g. modulate, switch, amplify, covert, rectify, multiplex, phase shift, etc.) the one or more neuronal feedback signals received from the transmitter module 1010 or to generate the one or more neuronal feedback signals based on the signal parameters received from the transmitter module 1010.

The CLCBI device moo further comprises a wired receiver module 1030 that is configured to receive/obtain one or more sensor signals from one or more sensors (as discussed above), indicative of an action or movement of an individual (e.g. a distance measurement obtained from a motion tracking sensor device, acceleration data obtained from an accelerometer etc.). In the embodiment of FIG. 10 the sensor signals are not received wirelessly but are obtained via sensor signal leads 1020.

The neurostimulation device of the individual is configured to output and apply the generated and processed neuronal feedback signals to one or more electric contacts of a neurostimulation electrode (e.g. a DBS electrode or spinal cord stimulation electrode; not shown) to elicit the desired sensory percept.

The CLCBI device 1010 may also comprise a power source 1060 that, for instance may be a removable battery.

Similar to FIG. 1 discussed above, FIG. 11*a* and FIG. 11*b* illustrate an individual, e.g. a stroke patient, taking part in a behavioral training task such as a rehabilitation and recovery procedure. The individual has been implanted with a neuronal stimulation electrode 1101/1201 such as a DBS electrode or a spinal cord stimulation electrode that may have multiple independently controllable electric contacts.

The individual may be further equipped with a neuronal stimulation device 1105/1205, that may be an IGB implanted under the skin if the individual. The neuronal stimulation device 1105/1205 may be in wireless communication 1104/1204 (e.g. via a Bluetooth, WI-FI, NFC, etc.) with a control device/pocket processor 1103/1203, that may be implemented by a dedicated signal and data processing device, a smartphone or a similar electronic information processing device. Depending on implementation details the devices provided by the present invention may be implemented via application specific hardware and/or software modules comprising circuitry and/or software instructions to implement the devices and systems according to the present invention.

As discussed above with reference to FIGS. 9 and 10 the various modules of the CLCBI device provided by the present invention may be implemented by the control device 1103/1203 or the neuronal stimulation device 1105/1205 or by a combination thereof.

Similar to the behavioral training task discussed in detail above with reference to FIG. 1 the CLCBI device may be configured to receive sensor signals from a motion tracking camera 1107/1207 and a wearable accelerometer 1106/1206.

For instance, the individual's limb position may continuously be tracked during task performance. The tracking data may be used to determine whether the hand of the individual is moved into the vicinity of an object 1102/1202. Depending on the behavioral learning task, the individual may receive movement support information via the CLCBI device that may indicate whether the object 1102/1202 should be avoided (see FIG. 11*a*) or be manipulated (e.g. grasped, see FIG. 11*b*) by the individual. For instance, a neuronal feedback signal provided by the CLCBI device may have been associated with a specific sensory modality and location such as a tough sensation of increasing intensity on the upper arm of the individual (see 1108 in FIG. 11*a*) to indicate the degree of proximity to objects that should be avoided. In this manner, the CLCBI device is enabled to inform the individual when it comes close to a hot or dangerous object.

Another neuronal feedback signal provided by the CLCBI device may have been associated with a tough sensation of increasing intensity in the palm of the hand of the individual (see region 1208 in FIG. 11*b*), in order to indicate the degree of proximity to an object that is to be manipulated by the individual (e.g. to help a stroke patient to train drinking from a cup again)

Naturally, this approach may also be combined with further sensor signals such as a touch sensor on the surface of the cup or any of the sensor signals described in detail above.

The invention claimed is:

1. A closed loop computer brain interface (CLCBI) device for an individual comprising:
a receiver configured to obtain a sensor signal indicative of a movement or action of the individual;
a non-transitory memory storing a plurality of neuronal feedback signals configured to elicit a corresponding plurality of respective sensory percepts in a cortex of the individual via stimulating afferent sensory axons of a central nervous system targeting sensory neurons of the cortex of the individual, wherein the plurality of sensory percepts is linked to a plurality of respective movement support information through a training procedure carried out by the individual and thereby configured to indicate the plurality of movement support information to the individual;
a processor that is operably connected to the receiver and the non-transitory memory, wherein the processor is configured to:
access the non-transitory memory and determine, based on the obtained sensor signal, a first neuronal feedback signal of the stored plurality of neuronal feedback signals; and
provide the first neuronal feedback signal to stimulate the afferent sensory axons and elicit a first sensory percept in the cortex of the individual, wherein the first sensory percept elicited by the first neuronal feedback signal indicates first movement support information of the plurality of movement support information that is related to the obtained sensor signal to assist the individual with execution of the movement or action of the individual.

2. The CLCBI device of claim 1, wherein the action or movement of the individual is associated with a training task and the movement support information supports the individual with performing the training task.

3. The CLCBI device of claim 1, wherein the movement support information is configured to provide one or more of the following to the individual:
a distance indication relating to an object to be manipulated by the individual;
an orientation indication for the individual or a body part of the individual;
an indication of a geographic position of the individual;
a success or failure indication for a training task executed by the individual;
an indication, preferably continuous, of a desired or unwanted trajectory of a movement or action to be executed by the individual;
an indication quantifying a degree of deviation from a desired trajectory of a movement or action to be executed by the individual;
an indication designating a desired or unwanted object to be manipulated by the individual;
an indication to start of stop the execution of the movement or action; or
an indication to provide the individual with a non-verbal instruction related to the execution of a task.

4. The CLCBI device of claim 1, wherein the at least one sensor signal is indicative of at least one of the following:
a position, distance, and/or orientation of a body part of the individual with respect to a fixed reference frame and/or another body part of the individual, and/or an object to be manipulated by the individual;

a muscle tension, contraction and/or relaxation state of the at least one body part of the individual;

a flexion, extension, supination, pronation and/or rotation angle of a joint of the at least one body part of the individual;

a movement speed associated with the at least one body part; and a contact pressure between a portion of the at least one body part and an object to be manipulated by the individual.

5. The CLCBI device of claim 1, wherein the receiver is further configured to obtain training data indicative of a training task associated with the movement or action of the individual.

6. The CLCBI device according to claim 1, wherein the obtained sensor signal is received from at least one of the following sensor devices: a computer vision tracking device; a kinematic sensor device; a touch sensor; an acceleration sensor device; and an electromyography device.

7. The CLCBI device of claim 1, wherein the links between the plurality of sensory percepts and the plurality of respective movement support information are based at least in part on one or more of the following: conceptual or perceptive learning data for the individual; neuro-imaging data for the individual; electrophysiological measurement data for the individual; neuronal connectivity information for the individual; electric field simulation data for the neurostimulation device of the individual; and neuronal excitability model data for the individual.

8. The CLCBI device of claim 1, wherein the first neuronal feedback signal is characterized by a plurality of signal parameters including one or more of a signal waveform, a signal frequency, a signal polarity, a signal pulse shape, a signal amplitude, a signal pulse width, a burst frequency, a burst pulse count and/or a burst duration; and wherein different combinations of signal parameters correspond to different movement support information.

9. The CLCBI device of claim 1, wherein the first neuronal feedback signal is configured to elicit the first sensory percept in a portion of the cortex of the individual associated with a specific sensory modality; and wherein the portion of the cortex is one or more of the following: a somatosensory cortex area; an auditory cortex area; a visual cortex area; an olfactory cortex area; an entorhinal cortex area or components of the circuit of Papez.

10. The CLCBI device of claim 1, wherein the first neuronal feedback signal is configured to stimulate thalamocortical axons projecting from the thalamus to the sensory neurons of the cortex and/or wherein the first neuronal feedback signal is configured to stimulate afferent sensory axons of the spinal cord projecting, via mono-synaptic or multi-synaptic pathways, to the thalamus or the cortex of the individual.

11. The CLCBI device of claim 1,
wherein the CLCBI device further comprises a transmitter operably connected to the processor and configured to transmit the first neuronal feedback signal to a neurostimulation device of the individual.

12. The CLCBI device of claim 1,
wherein the CLCBI device further comprises a neuronal signal generator operably connected to the processor and configured to receive the first neuronal feedback signal from the processor.

13. The CLCBI device of claim 1,
wherein the training procedure comprises a pair learning procedure that concurrently provides respective movement support information and neuronal feedback signals to link the respective movement support information and the elicited sensory percept for the individual,
wherein the processor is further configured to perform the pair learning procedure for the individual that links, for the individual, the plurality of movement support information and the plurality of sensory percepts elicited by the stored plurality of neuronal feedback signals.

14. A non-transitory computer readable memory medium comprising program instructions, wherein:
the non-transitory computer readable memory medium stores a plurality of neuronal feedback signals configured to elicit a corresponding plurality of respective sensory percepts in a cortex of an individual via stimulating afferent sensory axons of a central nervous system targeting sensory neurons of the cortex of the individual, wherein the plurality of sensory percepts is linked to a plurality of respective movement support information through a training procedure carried out by the individual and thereby configured to indicate the plurality of movement support information to the individual,
wherein the program instructions are executable by a processor to:
obtain a sensor signal indicative of a movement or action of an individual;
access the non-transitory computer readable memory medium determine a neuronal feedback signal of the stored plurality of neuronal feedback signals based at least in part on the obtained sensor signal; and
transmit the neuronal feedback signal to a neurostimulation device or module of the individual to stimulate the afferent sensory neurons and elicit a first sensory percept in the cortex of the individual, wherein the first sensory percept elicited by the first neuronal feedback signal indicates first movement support information of the plurality of movement support information that is related to the obtained sensor signal to assist the individual with execution of the movement or action of the individual.

15. The non-transitory computer readable memory medium of claim 14,
wherein the action or movement executed by the individual is associated with a training task and the movement support information supports the individual with performing the training task.

16. The non-transitory computer readable memory medium of claim 14, wherein the movement support information is configured to provide one or more of the following to the individual:
a distance indication relating to an object to be manipulated by the individual;
an orientation indication for the individual or a body part of the individual;
an indication of a geographic position of the individual;
a success or failure indication for a training task executed by the individual;
an indication, preferably continuous, of a desired or unwanted trajectory of a movement or action to be executed by the individual;
an indication quantifying a degree of deviation from a desired trajectory of a movement or action to be executed by the individual;

an indication designating a desired or unwanted object to be manipulated by the individual;

an indication to start of stop the execution of the movement or action; or an indication to provide the individual with a non-verbal instruction related to the execution of a task.

17. The non-transitory computer readable memory medium of claim 14, wherein the at least one sensor signal is indicative of at least one of the following:

a position, distance, and/or orientation of a body part of the individual with respect to a fixed reference frame and/or another body part of the individual, and/or an object to be manipulated by the individual;

a muscle tension, contraction and/or relaxation state of the at least one body part of the individual;

a flexion, extension, supination, pronation and/or rotation angle of a joint of the at least one body part of the individual;

a movement speed associated with the at least one body part; or a contact pressure between a portion of the at least one body part and an object to be manipulated by the individual.

18. The non-transitory computer readable memory medium of claim 14, wherein the training procedure comprises a pair learning procedure that concurrently provides respective movement support information and neuronal feedback signals to link the respective movement support information and the elicited sensory percept for the individual, wherein the program instructions are further executable by the processor to perform the pair learning procedure for the individual that links, for the individual, the plurality of movement support information and the plurality of sensory percepts elicited by the stored plurality of neuronal feedback signals.

19. A method, comprising:

obtaining a sensor signal indicative of a movement or action of the individual;

storing, in a non-transitory computer-readable memory medium, a plurality of neuronal feedback signals configured to elicit a corresponding plurality of respective sensory percepts in a cortex of the individual via stimulating afferent sensory axons of a central nervous system targeting sensory neurons of the cortex of the individual, wherein the plurality of sensory percepts is linked to a plurality of respective movement support information through a training procedure carried out by the individual and thereby configured to indicate the plurality of movement support information to the individual; and by a processor:

accessing the non-transitory memory and determining, based on the obtained sensor signal, a first neuronal feedback signal of the stored plurality of neuronal feedback signals; and providing the first neuronal feedback signal to stimulate the afferent sensory axons and elicit a first sensory percept in the cortex of the individual, wherein the first sensory percept elicited by the first neuronal feedback signal indicates first movement support information of the plurality of movement support information that is related to the obtained sensor signal to assist the individual with execution of the movement or action of the individual.

20. The method of claim 19, wherein the action or movement of the individual is associated with a training task and the movement support information supports the individual with performing the training task.

* * * * *